United States Patent [19]
Chedid et al.

[11] Patent Number: 5,374,440
[45] Date of Patent: Dec. 20, 1994

[54] METHOD FOR CONTROLLING COOKIE GEOMETRY

[75] Inventors: Lisa Chedid, Monmouth Junction; Janet Hennessey, Succasunna, both of N.J.

[73] Assignee: Nabisco, Inc., Parsippany, N.J.

[21] Appl. No.: 996,419

[22] Filed: Dec. 23, 1992

Related U.S. Application Data

[63] Continuation-in-part of Ser. No. 804,140, Dec. 6, 1991, Pat. No. 5,258,197, which is a continuation-in-part of Ser. No. 624,056, Dec. 7, 1990, abandoned, which is a continuation-in-part of Ser. No. 410,161, Sep. 20, 1989, abandoned.

[51] Int. Cl.$^5$ ................................. A23L 1/10
[52] U.S. Cl. ................................. 426/549; 426/804
[58] Field of Search ................. 426/549, 804, 551

[56] References Cited

U.S. PATENT DOCUMENTS

| | | |
|---|---|---|
| 3,919,434 | 11/1975 | Tsen et al. |
| 4,122,206 | 10/1978 | Hoseney . |
| 4,344,969 | 8/1982 | Younquist .................. 426/549 |
| 4,584,203 | 4/1986 | DuVall ........................ 426/549 |
| 4,668,519 | 5/1987 | Dartey et al. . |
| 4,840,803 | 6/1989 | Polizzano ................... 426/549 |
| 4,873,098 | 10/1989 | Banks ......................... 426/549 |
| 4,892,745 | 1/1990 | Gage ............................ 426/549 |
| 4,961,941 | 10/1990 | Cocco ......................... 426/549 |
| 4,961,942 | 10/1990 | Cocco ......................... 426/549 |
| 4,965,076 | 10/1990 | Marten ....................... 426/549 |
| 4,965,077 | 10/1990 | Marten ....................... 426/549 |

OTHER PUBLICATIONS

Patton 1976 Biomedical Aspects of Lactation pp. 77–83 Pergamon Press New York.
Fuhr, R., Bakers Digest 36(4): 56–58, 78 (1962).
Mensink, R. P. and Katan, M. B., New Eng. Lour. Med., 323: 439–445 (1990).
Surgeon General's Report on Nutrition and Health, Prima Pub. Co., 1988, p. 98.

Primary Examiner—Carolyn Paden

[57] ABSTRACT

A method for controlling spread in cookies uses in the cookie dough a shortening comprising geometry-altering triglycerides bearing long $C_{16}$ to $C_{22}$ saturated fatty acid residues and short $C_2$ to $C_4$ acid residues. In a preferred embodiment, the triglycerides have a solid fat index of about 10% to about 70% between 15° and 30° C., and the long residues are a mixture containing at least about 75% stearic acid residues while the short residues are derived from a mixture of acetic and propionic acid, a mixture of acetic and butyric, or a mixture of acetic, propionic, and butyric acid. The method is especially adapted to reducing spread in cookies containing an ingredient that promotes spread such as polydextrose. Cookies prepared with polydextrose and geometry-altering triglyceride compositions are low in calories.

19 Claims, No Drawings

METHOD FOR CONTROLLING COOKIE GEOMETRY

RELATED U.S. APPLICATION DATA

This is a continuation-in-part of co-pending U.S. application Ser. No. 804,140, filed Dec. 6, 1991, now U.S. Pat. No. 5,258,197 hereby incorporated in its entirety by reference, which was a continuation-in-part of U.S. application Ser. No. 07/624,056, filed Dec. 7, 1990, now abandoned, which was a continuation-in-part of U.S. application Ser. No. 07/410,161, filed on Sep. 20, 1989, now abandoned.

TECHNICAL FIELD

This invention relates to methods of altering cookie geometry.

Cookies are compounded to possess a certain flavor balance, cell structure, appearance, color, texture and aftertaste. These properties are related to cookie geometry, i.e., spread and stack height. Cookie geometry is a function of the total availability of water (Fuhr, R., *Bakers Digest* 36(4): 56–58, 78 (1962)), the kind of milling and level of flour employed in the cookie, the sugar type and level, the water content, the protein content, the liquidity of the shortening, mixing temperature, baking temperature, atmospheric pressure, added ingredients, etc. Spread and stack height must be controlled in commercial baking operations so that the finished goods exhibit consistent quality with a minimum of production losses and the cookies have uniform diameters and thicknesses that can be packaged easily. This is especially true where the packages are formed on continuous wrapping machines because the bottom seam must have correct overlap to seal, and this is a function of cookie size. Product standardization also allows cookies to be sold by count as well as weight, an advantage to both consumers and manufacturers.

It is desirable to have methods for modulating cookie geometry without adversely affecting eating quality.

BACKGROUND ART

Most cookies are formulated to have a uniform stack height and some, but not excessive, spread. However, some ingredients such as certain flours and sweeteners, shredded coconut and coarse oats or oatmeal without fines, and soft to liquid shortenings increase spread, as does the high moisture content of soft cookies, and the increase can be detrimental to product quality. For example, cookies formulated with desirable polyunsaturated fat, which lowers plasma cholesterol (*Surgeon General's Report on Nutrition and Health*, Prima Pub. Co., 1988, page 98), yield soft doughs that spread excessively when baked. Cookies formulated with certain sugar substitutes and bulking agents, such as polydextrose, also spread excessively. Cookies that spread too much cannot be filled into standard packages.

Polyunsaturated fats can be hardened by hydrogenation to form a product having more solids that spreads less, but the process yields fats bearing significant amounts of trans-unsaturated fatty acid residues. These have been recently shown to raise low density lipoprotein serum cholesterol levels and to lower high density lipoprotein serum cholesterol levels in adults fed fats having these acids (Mensink, R. P., and Katan, M. B., *New Eng. Jour. Med.*, 323: 439–445 (1990)).

Corn, sorghum, and millet flours have been reported to decrease cookie spread, but the cookies are generally tough, hard and gritty with a mealy texture and taste (U.S. Pat. No. 4,122,206 to Hoseney). The patent suggests that if the flours are hydrated, partially dehydrated and mixed with lecithin, superior results are achieved. The process involves controlled conditions, several steps and considerable time, however. Hydration requires at least 30 minutes, preferably 3 to 15 hours, and afterwards care must be taken during dehydration, which is preferably accomplished by passing dry room temperature or heated air over the grain, so that the grain starch is not gelatinized.

The geometry of reduced-shortening, preferably protein-supplemented, baked products is preserved in U.S. Pat. No. 3,919,434 to Tsen and Hoover, which incorporates from 0.1 to 3% by weight either sodium or calcium salts of acyl lactylates of $C_{14}$ to $C_{22}$ fatty acids (preferably sodium stearoyl-2-lactylate) in the batter or dough. The compositions require at least one lactylate additive, and, because of its preparative procedure, it can contain, as contaminants, unreacted lactic acid, fatty acids, and other lactylates including polylactylates, and their salts.

Another additive is disclosed in U.S. Pat. No. 4,873,098 to Banks, et al., which describes a method for controlling oven spread by including in the cookie dough, in an amount of from about 2 to 20% by weight based upon the weight of the flour, a cold water swelling granular starch material having a cold water solubility of at least 50%, preferably at least 70%. The cold water soluble granular starch material must have specified properties to function properly, and the amount used, which depends upon the amount and type of flour, the amount of moisture, and the amount and type of humectant in the dough, is significant, ranging from about 5 to about 10 parts by weight of the flour in the examples. This adds to preparation costs.

The size and texture of baked cookies have been controlled by adding the required amount and types of sugar in varying portions at different points in the sequence of ingredient addition during dough mixing (U.S. Pat. No. 4,668,522 to Cappel and Cronemiller). One portion of sugar is added with the liquid ingredients, a second portion is added after preparation of a slurry containing shortening and liquid ingredients, and a third portion is added as a final step after all the other liquid and dry ingredients have been combined. The process is quite complicated, and applicable only to baked cookies made from doughs having two types of sugars.

A multi-component leavening system and an edible alkaline agent are used to provide a pleasing open-celled texture and appearance in cookies containing polydextrose, an emulsifier, and a cellulosic bulking agent in a reduced flour, sugar and shortening recipe (U.S. Pat. No. 4,668,519 to Dartey and Biggs). The leavening system comprises specified levels of an edible bicarbonate and/or carbonate salt and a delayed-action acidifier that releases about 50% of the leavening gas during baking. Like the Cappel and Cronemiller disclosure, the Dartey and Biggs formulation and procedure for making the cookies are complicated.

It would be desirable to control cookie geometry when ingredients that can contribute to excessive spread are included in the cookie recipes. It would also be desirable to have methods of modulating cookie geometry without the use of additives or special processing equipment and techniques.

DISCLOSURE OF THE INVENTION

It is an object of the present invention to provide a method for modulating cookie geometry by varying the fats in the shortening component.

Another and more specific object of the invention is to provide a method for controlling cookie spread, while providing acceptable cookie stack height, in formulations containing an ingredient that increases spread such as polydextrose.

A further object of the invention is to provide cookie shortenings and cookies low in calories and low in or free of trans-unsaturated fatty acids.

These and other objects are accomplished by the present invention, which provides a method for controlling biscuit geometry in the preparation of cookies. Preferred embodiments control spread and stack height in recipes containing a spreading ingredient, providing acceptable and uniform baked cookies without adversely affecting dough viscosity or processability.

The method employs geometry-altering triglycerides bearing long $C_{16}$ to $C_{22}$ saturated fatty acid residues and short $C_2$ to $C_4$ acid residues (hereafter referred to as "short/long triglycerides") in the fat ingredient of the cookie dough. Especially preferred are triglycerides having a solid fat index of about 10% to about 70%, more narrowly about 30 to about 40% between 15° and 30° C. Preferred triglycerides bear long residues derived from a mixture containing at least about 75% stearic acid, and the short residues are derived from a mixture of acetic and propionic acid, a mixture of acetic and butyric, or a mixture of acetic, propionic and butyric acid.

In preferred embodiments, cookie spread and stack height are controlled by admixing geometry-altering triglycerides with other dough ingredients including, optionally, a spreading ingredient such as polydextrose or a polyunsaturated fat, forming the dough into pieces and baking the dough pieces. Where the dough contains a spreading ingredient, short/long triglycerides are added in amounts effective to control cookie geometry.

GENERAL DESCRIPTION OF THE INVENTION

This invention is based upon the finding that spread and stack height of baked cookies can be engineered by using certain fats in the shortening component of the cookie dough without adversely affecting dough processing characteristics or the quality of the baked product. Surprisingly, certain triglycerides in the fat component can decrease spread in recipes containing ingredients that give rise to spread without affecting the viscosity of the dough or the eating quality of the baked cookie.

The methods of this invention employ geometry-altering shortenings that comprise a fat enriched with short/long triglycerides bearing both long, saturated $C_{16}$ to $C_{22}$ fatty acid residues and short $C_2$ to $C_4$ acid residues. Preferred short/long triglycerides exhibit a solid fat content of about 10% to about 70%, preferably about 30% to about 40%, between 15 and 30° C. In preferred embodiments, the short acid complement preferably comprises a mixture of short acid residues such as a mixture of acetic and propionic acid, a mixture of acetic and butyric acid, or a mixture of acetic, propionic and butyric acid. In these embodiments, the long fatty acid residues generally contain predominantly, i.e., at least about 75%, and in many embodiments at least about 90%, stearic acid residues.

Denoting the aliphatic portion of the long fatty acid substituent as L and the short as S, the geometry-altering shortening compositions of this invention contain fats comprising a mixture of SSL, SLS, LLS, and LSL species described by the following formulae:

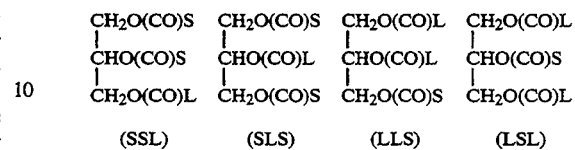

where
each L, independently, is a long chain saturated aliphatic group having between 15 and 21 carbons, derived from a fatty acid having 16 and 22 carbons; and
each S, independently, is a short chain group having 1 to 3 carbons.

In many embodiments, at least about 60 to about 70 mole % of the groups in the total triglyceride mixture are short chain groups. An especially preferred embodiment contains at least about 64 to about 67 mole % short chain groups in the total mixture. Many of these fats contain at least about 75% SSL/SLS species.

Depending upon the preparative procedure, the triglyceride mixtures may also contain triglycerides of the formulae

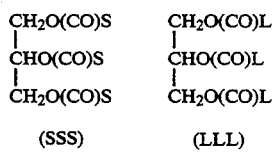

where S and L are as defined above.
However, preferred mixtures contain essentially no SSS and less than about 4% LLL.

Short acid residues have 2 to 4 carbons. Short residues are derived from carboxylic acids of the formula SCOOH, where S is a short chain aliphatic group having 1 to 3 carbons. Acylation of a glycerol hydroxyl by acid SCOOH results in the attachment of short chain S to the glycerol backbone by means of an ester linkage (—O—(CO)—). As used herein, the term "acid residue" refers to an acyl group comprising a short chain portion, here S, and a carbonyl group.

Short chain S may be straight or branched. Short chain S may be derived from any synthetic or natural organic acid including, but not limited to acetic (ethanoic), propionic (propanoic), butyric (butanoic), and the like acids. As used herein, chemical names include isomeric variations; for example, "butyric acid" includes normal-butyric acid (butanoic) and iso-butyric (2-methylpropanoic) acid, and so forth.

In preferred embodiments, the S moieties are derived from a mixture of acids such as, for example, a mixture of acetic and propionic, a mixture of acetic and butyric, or a mixture of acetic, propionic and butyric acid residues. Many embodiments contain predominantly propionic acid in the short acid component. In one embodiment, geometry control is achieved by employing a mixture of about 10 mole % to 40 mole %, more narrowly about 10 mole % to about 15 mole %, acetic acid residues and about 60 mole % to about 90 mole %, more narrowly about 85 mole % to about 90 mole %, propionic acid residues in the short chain component. Another embodiment achieves geometry control by employing a mixture of about 15 mole % to about 20 mole %, more narrowly about 20 mole %, acetic acid residues, about 35 mole % to about 45 mole %, more narrowly about 40 mole %, propionic acid residues, and about 35 mole % to about 45 mole %, more narrowly about 40 mole %, butyric acid residues.

The long saturated pendant groups are derived from fatty acids of the formula LCOOH, where L is a saturated aliphatic group having 15 to 21 carbons. L groups may be derived from any synthetic or natural, straight or branched saturated organic acid including, but not limited to, palmitic (hexadecanoic), stearic (octadecanoic), arachidic (eicosanoic), behenic (docosanoic), and the like acids.

L groups may be derived from hydrogenated, unsaturated long groups. These are derived by hydrogenating unsaturated acids of the formula UCOOH, where U is a $C_{15}$ to $C_{19}$ unsaturated group, including, but not limited to, palmitoleic (9hexadecenoic), oleic (cis-9-octadecenoic), elaidic (trans-9-octadecenoic), vaccenic (trans-11-octadecenoic), linoleic (cis, cis-9,12-octadecedienoic), linolenic (9,12,15-octadecatrinoic and 6,9,12-octadecatrienoic), eleostearic (9,11,13octadecatrienoic), arachidonic (5,8,11,14-eicosatetraenoic), and the like acids.

The various L and U groups can be derived from mixtures of fatty acids obtained from natural oils such as soybean, safflower, sunflower, sesame, peanut, corn, olive, rice bran, mustard seed, cottonseed, poppyseed, rapeseed, marine, meadowfoam and the like oils; fats such as babassu nut oil, palm oil, palm kernel oil, tallow, lard, shea butter, dairy butter; or plant waxes such as jojoba. Fat mixtures and/or fractions, crystallized fats, interesterified fats and mixtures of these may also be employed.

Mixtures of L groups are preferably employed and these may be derived from oils and fats that are hydrogenated, most preferably fully hydrogenated. Hydrogenated fats having at least about 75%, stearic acid residues such as, for example, hydrogenated peanut oil, hydrogenated olive oil, hydrogenated soybean oil, hydrogenated sesame oil, and hydrogenated corn oil are especially desirable for some embodiments. Other embodiments have L moieties derived from fats having at least about 90% stearic acid residues, such as hydrogenated sunflower oil, hydrogenated safflower oil and hydrogenated canola.

Preferred hydrogenated feedstocks are low in palmitic acid. This maximizes the health benefits of the cookies made according to the method of this invention, since lauric, myristic, or palmitic acid residues have recently shown to increase plasma cholesterol concentrations (Bonanome, A., and Grundy, S. M., *New Eng. Jour. Med.* 318: 1244–1248 (1988)).

Geometry-altering shortening fats may be prepared using synthetic procedures known to those skilled in the art, such as, for example, directly esterifying glycerol or glycerol esters with fatty acids, fatty acid halides (notably chlorides) or fatty acid anhydrides, transesterifying glycerol with fatty acid esters, or interesterifying long and short chain triglycerides for such time and under such conditions that the triglycerides bearing long and short residues form. Starting materials for triglyceride preparations may be obtained commercially or isolated from natural sources. Alternatively, component triglycerides may be isolated from natural or processed fats or oils, or fractions thereof.

Some desirable triglyceride mixtures are prepared using a random interesterification of triacetin and tripropionin, and optionally, tributyrin with a substantially hydrogenated fat having at least about 90% stearic acid residues such as hydrogenated canola. Mixtures and fractions of triglycerides may also be employed, such as those derived by blending the products of different interesterifications. Example preparations are illustrated hereafter.

Isolated or prepared triglycerides are purified using techniques known to those skilled in the art. These include, but are not limited to, steam deodorization, fractional crystallization, distillation, chromatography, and the like. In some embodiments, geometry-altering shortening fats of this invention are prepared by blending products purified by one means, e.g., steam deodorization, with fractions obtained in purifications using other means, e.g., fractional crystallization and/or distillation.

BEST MODES FOR CARRYING OUT THE INVENTION

In the practice of this invention, geometry-altering fats bearing long, saturated $C_{16}$ to $C_{22}$ fatty acid residues and short $C_2$ to $C_4$ acid residues as defined above and having a solid fat index of about 10% to 70%, more narrowly about 30% to 40%, between 15° and 30° C. are incorporated in the shortening component of cookies. In cookie recipes having a tendency to spread such as those containing polydextrose, the fats are incorporated in amounts effective to reduce spread. In a preferred method of the invention, at least about 75% of the L groups in the short/long triglycerides are derived from stearic acid, and the S groups contain a mixture of residues such as acetic and propionic acid residues, acetic and butyric acid residues, or acetic, propionic, and butyric acid residues.

As used herein, the "solid fat index" of desirable fats of this invention refers to the percentage of a fat that exists in crystalline form at a given temperature. Solid fat indices (herein abbreviated S.F.I.) are determined using dilatometry according to A.O.C.S. Method Cd 10-57, and are reported at 50° F. (10° C.), 70° F. (21.1° C.), 80° F. (26.7° C.), 92° F. (33.3° C.), and 100° F. (37.8° C.).

By "geometry-altering" triglycerides is meant that, when used in cookie shortening, the triglyceride mixture affects the spread and, in most cases, the stack height of cookies when these measurements are compared to control cookies made with conventional shortening. By "cookie spread" is meant the horizontal movement in the cookie dough mass as it is subjected to oven baking conditions. By "stack height" is meant the vertical movement of the cookie dough mass during baking.

By the term "cookie" is meant any of a variety of small cakes, usually flat or slightly raised, that are prepared by rolling and cutting, dropping, or shaping dough and then baking it, or by cutting dough into pieces after baking. A cake is any baked product made from a sweetened dough or batter, including conventional types containing flour and other ingredients, leavened with yeast, baking powder, or beaten egg whites and, optionally, iced.

Cookies made according to the method of this invention generally have a starch component in addition to the shortening component. The starch typically comprises a flour such as wheat flour. Potato, rice, or other cereal flours such as corn, oats, rye, mixtures thereof, other starch ingredients known to the skilled artisan, ground nuts and nut meals, and the like can be used instead of, or in addition to, flour.

Cookies prepared according to the method of the present invention typically also comprise a natural or artificial sweetener. Natural sweeteners include sugar (sucrose), glucose, fructose, and maltose. Artificial sweeteners include 1-aspartyl-1-phenylalanine methyl ester (commercially available as aspartame or Nutri-Sweet TM), saccharine, cyclamate, L-alpha-aspartyl-N-2,2,4,4-tetramethyl-3-thiethanyl-D-alaninamide hydrate (commercially available as Alitame TM), 4,1′,6′-trichloro-4,1′,6′-trideoxygalactosucrose (commercially available as Sucralose TM) and the potassium salt of 6-methyl-3,4-dihydro-1,2,3-oxathiazin-4-one-2,2-dioxide (commercially available as acesulfame-K TM), or a mixture of these.

A bulking agent can be employed as a sugar replacement. Bulking agents contribute little or no sweetness to the product, and preferably contribute little or no taste. Preferred bulking agents are carbohydrates, which are most preferably at least partially non-digestible. Typical bulking agents which are suitable for use in these instances include polydextrose (commercially available as Litesse TM), isomalt (commercially available as Palatinit TM), isomaltulose (commercially available as Palatinose), polyglucose, polymaltose, carboxymethyl-cellulose, microcrystalline cellulose, cellulose gel, arabinogalactan, fructooligosaccharide (available as Nutraflora TM and Raftilose P95 TM), galactooligosaccharide, glucooligosaccharide, 4-O-(beta-galactosyl)-D-sorbitol (available as Lactitol TM), polyethylene glycol, and D-mannitol, as well as mixtures or combinations of any of these. When bulking agents are used, high intensity artificial sweeteners are commonly added at a low level to contribute sweetness.

Cookies made according to the method of this invention typically also contains a flavoring, e.g., vanilla, and salt. Cookies can also contain milk solids, eggs, cocoa, colorings, spices, leavening agents, chocolate or other flavored chips, fruits and nuts, browning agents, emulsifiers, mold, bacteria, yeast and oxidation inhibitors and the like. Aqueous ingredients such as water, milk, or fruit juices may be employed in some embodiments. Cookies can be filled, frosted or enrobed after baking.

The geometry-altering fats may be incorporated either alone, or in combination with another fat and/or fat mimetic, into any cookie. Other fats include butter, cocoa butter, natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters, neoalkyl esters, polyglycerol esters, malonate esters, propoxylated glycerols, retrofats, carboxy/carboxylates, polyvinyl alcohol esters and the like.

In a generalized process for manufacturing cookies, shortening is mixed with sweetener and then other ingredients, and the mixture is deposited, extruded, molded or rolled out and cut before placement on pans, sheets, or oven bands. The cookie dough is then baked under normal conditions known to the skilled artisan. Preferred doughs exhibit a viscosity that allows them to be easily processed with conventional equipment.

A variety of different cookie spreads and stack heights can be achieved using the method of this invention. For example, in comparison tests, using short/long triglycerides as the sole shortening component in cookies reduces spread by at least about 10%, often at least about 12 to 15% as compared to cookies containing conventional shortening. Stack height can be increased by at least about 5% to 15%, and increases of about 25 to 60% can be achieved using the method of this invention. More viscous doughs generally exhibit greater stack heights. Where short/long triglycerides are employed in the shortening component of a cookie containing an ingredient that spreads, such as bulking agents, shredded coconut, coarse oats, oatmeal without fines, or polyunsaturated fats, cookie geometry approximating control cookies can be achieved, or different cookie geometries can be engineered.

Since geometry-altering triglycerides are lower in calories than conventional fats, an important advantage of the invention is that reduced calorie cookies can be formulated using the method of this invention. This effect can be enhanced by using other low calorie ingredients in the recipes. For instance, where short/long triglycerides are used to modify the geometry of reduced calorie cookies containing artificial sweeteners or bulking agents so that the final products resemble full calorie cookies, the final product is lower in calories than the original reduced calorie cookie. In a preferred embodiment employing polydextrose, for example, using the method of this invention increases calorie reduction in polydextrose-containing cookies.

Another important advantage of the invention, as has been mentioned, is that spread can be reduced in cookie compositions containing spreading ingredients such as poly-unsaturated oils or polydextrose, resulting in cookies having a controlled geometry and/or conventional spread. It is a further advantage that cookies made using shortening according the method of the invention improve cohesiveness of the product. This feature is especially advantageous in recipes incorporating polydextrose as a bulking agent because the cookies produced are less fragile.

Another advantage of the invention is that cookies made using preferred embodiments are low in trans unsaturation. Moreover, because preferred geometry-altering triglycerides contain little or no unsaturation, cookies made with them are resistant to oxidation, and do not become rancid as quickly as ordinary ones.

Cookie doughs and cookies made using the method of this invention exhibit a number of other desirable characteristics. Uncooked doughs made with the geometry-altering triglycerides of this invention are more cohesive than doughs made with conventional shortening, so the doughs stick less to processing machinery (bowls, beaters, paddles, cutters) than doughs made with conventional shortenings. Moreover, the doughs are mechanically strong, maintaining their structural integrity on being rolled or sheeted out, and dough blanks remain whole during processing. Baked products having short-/long triglycerides in their shortening components also maintain their structural integrity, which is a special advantage, as has been mentioned, where ingredients that increase product fragility such as polydextrose are employed in the recipes.

Another advantage of the invention is that cookies employing some geometry-altering shortenings melt away faster in the mouth than products prepared with conventional shortenings. This contributes to the gustatory satisfaction of eating products prepared with them.

EXAMPLES

The following examples are presented to further illustrate and explain the present invention and should not be taken as limiting in any regard. Unless otherwise indicated, all parts and percentages are by weight, and are based on the weight at the particular stage of the processing being described.

As set out above, solid fat indexes are determined using dilatometry according to A.O.C.S. Method Cd 10-57 (1989). Fatty acid analyses are determined using proton nuclear magnetic resonance and are expressed as mole percent. Mettler dropping points (M.D.P.) are determined using a Mettler Thermosystem FP 800 following A.O.C.S. Method Cc 18-80 (1989).

Fat product analysis using supercritical fluid chromatography (S.C.C.), separating and quantifying the mixture components, generally employ a standard procedure. After filtering through a 0.45 micron filter, 0.1 ul of a 30 to 50 mg/ml sample is injected onto a 1×100 mm Deltabond Cyano ™ column from Keystone Scientific in a Suprex Model 200 A S.C.C. having an S.C.C.-grade carbon dioxide mobile phase and an oven temperature of 125° C. A linear pressure gradient of 100 to 300 atmospheres is applied over a course of 20 minutes (i.e., 10 atm/min), followed by a hold at 300 atmospheres for 10 minutes. A flame ionization detector at 400° C. detects emerging mixture components run against an internal standard of methyl tetradecanoate (10 to 12 mg/mL) in methylene chloride. External standards of mono-, di-, and tristearin (~10 mg/mL each) are run under identical conditions. Using these peak areas, the peak areas of the sample are normalized, added together, and divided by the total to obtain percentages of LSS & SLS, LLS & LSL, and LLL in the short/long mixtures.

Example 1

This example illustrates the preparation of a number of fats for use as cookie shortenings in the method of this invention. The fats are prepared by randomly interesterifying 1 molar equivalent hydrogenated canola (899 g refined, low erucic rapeseed oil containing 4% palmitic acid, hydrogenated at 180° C. and 60 lbs hydrogen until the Iodine Value (IV) is ≦3) with different molar equivalents of triacetin and tripropionin. The reactants are heated in the presence of 0.2 to 0.3% sodium methoxide to ~110° C. with agitation under a vacuum for about half an hour until color develops. (The M.D.P. may be checked at this time, and the reaction continued if the M.D.P. has not dropped sufficiently.) Phosphoric acid (~0.2 to ~0.5%, at least twice the amount of sodium methoxide) is added to stop the reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The products are cooled to 80° C., filtered, bleached, and steam deodorized at 210° C. for 2 to 3 hours.

Fat product A is prepared by randomly interesterifying 1 mole triacetin and 11 moles tripropionin with 1 mole hydrogenated canola and steam deodorizing using this procedure. Likewise, fat product B is prepared by interesterifying 3 moles triacetin and 9 moles tripropionin, C, by interesterifying 6 moles triacetin and 6 moles tripropionin, D, by interesterifying 9 moles triacetin and 3 moles tripropionin, and E, by interesterifying 11 moles triacetin and 1 mole tripropionin, each with 1 mole hydrogenated canola.

Using fat analysis methods outlined above, the following data are collected on fat products A through E:

|        |         | A       | B       | C       | D      | E      |
|--------|---------|---------|---------|---------|--------|--------|
| M.D.P. |         | 27.2° C.| 26.7° C.| 29.8° C.|        | 35° C. |
| S.F.I. | 50° F.  | 60.9%   | 49.2%   | 61.2%   | 65.8%  | 64.4%  |
|        | 70° F.  | 40.1%   | 25.2%   | 49.8%   | 61.7%  | 62.4%  |
|        | 80° F.  | 5.9%    | 4.0%    | 32.4%   | 50.0   | 58.7%  |
|        | 92° F.  | 0       | 0       | 0       | 0.3%   | 28.5%  |
|        | 100° F. | 0       | 0       | 0       | 0      | 0.4%   |
| S.C.C. | SSL/SLS | 84.8%   | 88.0%   | 84.4%   | 87.9%  | 82.8%  |
|        | LLS/LSL | 14.4%   | 11.4%   | 13.8%   | 11.6%  | 16.1%  |
|        | LLL     | 0.8%    | 0.7%    | 1.8%    | 0.5%   | 1.1%   |

Example 2

This example compares and contrasts the geometry and appearance of cookies prepared using Fat Products A through E of Example 1 with control cookies made using a commercially available (Centrasoy ™) hydrogenated soybean oil shortening. Using differential scanning calorimetry, at room temperature Fat Products A and B are closest to the control shortening value of about 50% solids.

| To prepare the cookies, mix | grams |
|---|---|
| fine granulated sugar | 72.0 |
| brownulated brown sugar | 22.5 |
| nonfat dry milk | 2.3 |
| salt | 2.8 |
| sodium bicarbonate | 2.3 |
| and then add | |
| control or test shortening | 90.0. |
| Add high fructose corn syrup | 3.4 |
| then ammonium bicarbonate | 1.1 |
| and vanilla extract | 0.34 |
| to water | calculated* |
| and add the water mixture to the shortening mixture. | |
| Add flour | calculated* |

*g flour = {(100-13% moisture basis)/(100-flour moisture %)}*225 g
g water = 225 g - g flour added + 49.5

Sheet and cut the dough according to AACC Method 10-22. Bake at 400° F. for 10 minutes in a National reel test bake oven.

Dough viscosity is measured using a Stevens-LFRA ™ texture analyzer. Immediately after preparing the dough, 109 grams are added to the LFRA cup and compressed to a constant volume. A spherical probe is then plunged into the dough 15 mm at a rate of 2 mm/sec. Five measurements are taken for each dough and the average load value (grams) is reported.

During baking, the dough blank weights and cookie weights are measured and recorded. The following equation is then used to calculate the percent weight loss during baking:

$$\text{weight loss} = 100*(dbw - cw)/dbw$$

where dbw = dough blank weight and cw = cookie weight. Final cookie moisture measurements are made using a Computrac ™ set at 150° C. Three runs of each sample are tested and an average moisture in % is recorded.

After baking, cookie geometry is measured. Using a micrometer, the cookie diameter/spread (mm) are measured on at least 3 cookies in 4 locations. An average value is obtained and reported as an average cookie diameter. Four cookies are then stacked and the stack height is measured. Average cookie height is then obtained by dividing by the number of cookies. The baked cookies exhibit satisfactory product color as evaluated using a Minolta Chroma ™ meter model CR-210.

Using these methodologies, the following data about the dough and the cookies made with Fat Products A to E are obtained

|  | Control | A | B | C | D | E |
| --- | --- | --- | --- | --- | --- | --- |
| Dough LFRA | 112 | 180 | 136 | 296 | 717 | 1105 |
| Weight Loss | 12.3% | 8.6% | 6.6% | 9.3% | 10.5% | 9.3% |
| Moisture | 5.6% | 8.6% | 9.6% | 7.7% | 10.6% | 7.6% |
| Diameter | 82.6 mm | 70.8 mm | 71.5 mm | 71.2 mm | 73.4 mm | 80.1 mm |
| Height | 9.2 mm | 11.8 mm | 10.2 mm | 13.6 mm | 14.4 mm | 15.5 mm |

Since desirable processability LFRA values for the doughs should fall between about 100 to about 300, mixtures A, B, and C are acceptable shortenings in this cookie recipe, but fat products D and E yield doughs that are too stiff.

All the cookies formulated with fat products A to E yielded cookies with reduced spread in comparison to the control, but cookies prepared with fat products A, B, and C exhibit more pronounced spread reduction. Compared to the control cookies, spread decreases by about 13 to 14% in cookies prepared with Fat Products A, B, and C, but only by about 3 to 11% in cookies prepared with Fat products D and E.

Stack heights, on the other hand, are increased by about 56 to 68% in the cookies containing fat products D and E, but only about 11 to 48% with fat products A to C.

Texture of the baked cookies is evaluated using an Instron ™ 4501 Universal Testing machine, which punctures the cookies and measures resistance to a small probe. Values for stress and moduli, which can be correlated with hardness, fracturability and/or brittleness, are calculated based on the resistance force versus distance. Using this technique with the control and samples A to E, it is found that textural attributes from cake-like to a dense snap cookie can be achieved using the method of this invention.

Example 3

This example illustrates that the selection of long chain moieties in the preparation of fats used in the method of this invention affect cookie geometry. Cookies prepared with fats having essentially the same complement of short acid residues but having a different complement of long acid residues are compared with each other and with control cookies.

Two fat products are prepared and steam deodorized as described in Example 1 above. Fat product F, prepared by randomly interesterifying 1 mole triacetin and 11 moles tripropionin with 1 mole substantially fully hydrogenated soybean oil, has a M.D.P. of 28.1° C. and a S.F.I. of 63.7% at 50° F. 45.1% at 70° F., 5.1% at 80° F., and 0% at 92° F. Fat product G, prepared by randomly interesterifying 1 mole triacetin and 11 moles tripropionin with 0.9 moles hydrogenated canola and 0.1 moles substantially fully hydrogenated high erucic rapeseed oil, has a M.D.P. of 31° C. and a S.F.I. of 64.5% at 50° F. 53.1% at 70° F., 26.2% at 80° F., and 0% at 92° F.

Using the cookie recipes and comparative methodologies of Example 2, the following data about the dough and the cookies made with Fat Products A, F, and G are compared to the Example 2 control:

|  | Control | A | F | G |
| --- | --- | --- | --- | --- |
| Dough LFRA | 112 | 180 | 165 |  |
| Weight Loss | 12.3% | 8.6% | 9.4% | 8.4% |
| Moisture | 5.6% | 8.6% | 6.2% |  |
| Diameter | 82.6 mm | 70.8 mm | 81.3 mm | 77.0 mm |
| Height | 9.2 mm | 11.8 mm | 10.5 mm | 11.6 mm |

Sample A cookies prepared with triglycerides bearing hydrogenated canola (low erucic rapeseed) L residues, which contain about 96% stearic acid moieties, and acetic and propionic acid S residues, exhibit 14% less spread over the control. Sample F cookies containing fats derived from interesterifying the same reactants in the same proportions except that some high erucic rapeseed is admixed with low erucic rapeseed in the long chain feedstock and thus has slightly less stearic acid residues, exhibit only 7% less spread. Yet sample F cookies made with the same complement of S residues and L residues derived from hydrogenated soybean, which has more palmitic and less stearic than rapeseed, exhibits only a 2% decrease in spread.

Stack heights follow the same pattern. Fat product A (canola) cookies have a stack height 28% greater than the control, and fat product G (low and high erucic rapeseed) cookies are 26% higher, but fat product F (soybean) cookies are only 14% higher than control cookies.

Example 4

This example illustrates that the selection of short chain moieties in the preparation of fats used in the method of this invention also influences cookie geometry. Cookies prepared with fats having essentially the same complement of long acid residues but having a different complement of short acid residues are compared with each other and with control cookies.

Four fat products are prepared and steam deodorized as described in Example 1 above. Fat product H, prepared by interesterifying 0.5 mole triacetin, 1 mole tripropionin, and 1 mole tributyrin with 1 mole hydrogenated canola, has a M.D.P. of 35° C. and a S.F.I. of 68.6% at 50° F., 63.2% at 70° F., 42.5% at 80° F., 4.6% at 92° F., and 4.6% at 100° F. Fat product I, prepared by interesterifying 2.4 moles triacetin, 4.8 moles tripropionin, and 2.8 moles tributyrin with 1 mole hydrogenated canola, has a M.D.P. of 26.8° C. and a S.F.I. of 63.3% at 50° F., 36.1% at 70° F., 1.0 at 80° F., and 0 at 92° F. Fat product J, prepared by interesterifying 0.7 moles triacetin, 1.4 moles tripropionin, and 1.4 moles tributyrin with 1 mole hydrogenated canola, has a M.D.P. of 31.3° C. and a S.F.I. of 67.8% at 50° F., 56.5% at 70° F., 29.6% at 80° F., and 0% at 92° F.

Fatty acid analysis (using proton nuclear magnetic resonance) of another lot of Example 1 Fat Product A is compared to these fat products, yielding the following molar percentages:

| acid | A | H | I | J |
|---|---|---|---|---|
| acetic | 7% | 11% | 13% | 12% |
| propionic | 57% | 24% | 28% | 25% |
| butyric |  | 24% | 26% | 25% |
| long | 36% | 41% | 33% | 39% |

Cookies are prepared and analyzed as set out in Example 2 above, yielding the following information about dough viscosity, cookie geometry, and moisture content of samples H, I, and J compared with a hydrogenated soybean oil control:

|  | Control | H | I | J |
|---|---|---|---|---|
| LFRA | 149 | 790 | 151 | 286 |
| Weight Loss | 12.5% | 9.4% | 9.5% | 10.4% |
| Moisture | 5.1% | 6.9% | 8.9% | 6.9% |
| Diameter | 81.4 mm | 79.7 mm | 70.3 mm | 74.8 mm |
| Height | 9.0 mm | 11.0 mm | 10.5 mm | 9.5 mm |
| Stress* | 0.4 | 0.4 | 0.1 | 0.3 |
| Moduli* | 8.8 | 12.3 | 2.6 | 8.5 |

*kg/mm$^2$

Sample I has a dough with the best processability of the three test fat formulations, and sample H the poorest. Sample I also yields the most reduction in spread of the baked cookie: 14%. Samples H and J yield reductions of only 2% to 8%. It can be seen from the data in this series that increasing the propionic acid content somewhat results in less spread.

Similar results are achieved in a comparison of cookies made with shortenings having long chain residues derived from hydrogenated soybean oil rather than hydrogenated canola. Fat Product K is prepared by the random interesterification of 1 mole of hydrogenated soybean oil with 1.5 moles triacetin and 1.5 moles tripropionin as outlined in Example 1 above. The product has a M.D.P. of 36° C. and an S.F.I. of 71.9% at 50° F., 71.0% at 70° F., 64.7% at 80° F., 7.0% at 92° F., and 3.2% at 100° F. Fat Product L is prepared by interesterifying 1 mole of hydrogenated soybean oil with 2.5 moles tributyrin to obtain a product having a M.D.P. of 33.2° C. and a S.F.I. of 66.8% at 50° F., 36.9% at 70° F., 12.2% at 80° F., 7.7% at 92° F., and 6.9% at 100° F. cookies prepared with these and Fat Product F of Example 3 are compared with a control:

|  | Control | F | K | L |
|---|---|---|---|---|
| LFRA | 149 | 165 | 1101 | 173 |
| Weight Loss | 12.5% | 9.4% | 12.1% | 9.8% |
| Moisture | 5.1% | 6.2% | 6.5% | 7.8% |
| Diameter | 81.4 mm | 81.3 mm | 79.4 mm | 76.7 mm |
| Height | 9.0 mm | 10.5 mm | 12.0 mm | 10.0 mm |
| Stress* | 0.4 | 0.4 | 1.0 | 0.3 |
| Moduli* | 8.8 | 13.2 | 15.4 | 9.8 |

*kg/mm$^2$

All the test fat recipes yield cookies with greater stack height than the control. The test fat F cookies have spread similar to the control, but 17% greater stack height. Similarly, the test fat L cookies have 6% less spread and 11% greater stack height. Fat product K is difficult to process, but yields cookies with spread 2% of the control and stack height 33% greater than the control.

Example 5

This example illustrates how the shortenings of this invention can be used to reduce the excessive spread observed in cookies formulated with polydextrose as a sugar substitute.

Cookies are formulated (using the same recipe), cut and measured as set out in Example 2. The samples compared and contrasted are control cookies prepared with Centrasoy TM hydrogenated soybean oil shortening and sugar; cookies prepared with control shortening and polydextrose (Litesse TM obtained from Pfizer, denoted "PD" below) replacing the sugar (94.5 g, replacing both the brown and the white sugar components); cookies prepared with fat product A of Example 1 and sugar; cookies prepared with Fat Product A and polydextrose (PD+A); and cookies prepared with Fat Product A, polydextrose (56.7 g) and sugar (28.8 g white and 9 g brown), denoted PD+A+S.

The following results are obtained:

|  | Control | PD | A | PD + A | PD + A + S |
|---|---|---|---|---|---|
| Diameter | 81.0 mm | 85.2 mm | 72.0 mm | 77.6 mm | 75.3 mm |
| Height | 9.0 mm | 7.0 mm | 9.2 mm | 8.3 mm | 8.3 mm |

Cookies prepared with polydextrose and conventional shortening exhibit excessive spread and diminished stack height, whereas cookies formulated with fat product A have significantly less spread. Adding polydextrose to fat product A allow the spread and stack height to approach the control.

Example 6

This example illustrates how cookie geometry can be controlled at reduced shortening levels.

The cookie recipe of Example 2 is employed using full amounts and decreased levels of control or test shortening in otherwise identical recipes, and the cookies are compared to controls made with 100% Centrasoy TM as set out in Example 2. The test shortening is a different lot of Fat Product A. Polydextrose is used as a sugar substitute in one recipe as outlined below. The following results are obtained:

|  | Control | 90% Control | 75% Control | 50% Control |
|---|---|---|---|---|
| LFRA | 149 | 158 | 178 | 312 |
| Weight Loss | 12.5% | 13.2% | 12.2% | 8.4% |
| Moisture | 5.1% | 4.8% | 5.6% | 6.4% |
| Diameter | 81.4 mm | 81.4 mm | 81.5 mm | 74.1 mm |
| Height | 9.0 mm | 8.9 mm | 10.2 mm | 13.2 mm |
| Stress* | 0.4 | 0.5 | 0.4 | 0.9 |
| Moduli* | 8.8 | 10.1 | 9.6 | 22.1 |
|  | A | 90% A | 90% A + PG | 75% A | 50% A |
| LFRA | 130 | 234 | 134 | 226 | 142 |
| Weight Loss | 9.8% | 5.3% | 10.9% | 10.2% | 8.2% |
| Moisture | 6.4% | 8.4% | 7.5% | 8.2% | 6.2% |
| Diameter (mm) | 77.7 | 74.3 | 81.4 | 77.3 | 72.7 |
| Height (mm) | 11.2 | 13.7 | 10.7 | 12.0 | 15.07 |
| Stress* | 0.7 | 0.3 | 0.5 | 0.2 | 1.1 |
| Moduli* | 15.2 | 13.6 | 12.5 | 6.6 | 26.4 |

*kg/mm$^2$

The results are consistent with earlier examples. Cookies prepared with fat product A at diminished shortening levels of 50%, 75% and 90% exhibit reduced spread and a greater stack height compared to controls prepared with conventional shortening at the same levels. Cookies prepared with fat product A and polydextrose at shortening levels of 90% exhibit a geometry similar to control cookies.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

We claim:

1. A method for reducing spread in cookies having a fat ingredient comprising:
   (a) forming a dough by admixing other ingredients with geometry-altering triglycerides bearing both long $C_{16}$ to $C_{22}$ saturated fatty acid residues and short $C_2$ to $C_4$ acid residues in amounts effective to reduce spread in the baked cookie by use of said triglycerides;
   (b) forming the dough into pieces; and
   (c) baking the dough pieces.

2. A method according to claim 1 wherein the solid fat index of the triglycerides is between about 10% and about 70% between 15° and 30° C.

3. A method according to claim 2 wherein the solid fat index of the triglycerides is between about 30% and about 40% between 15° and 30° C.

4. A method according to claim 2 wherein the short acid residues in the triglycerides are selected from the group consisting of a mixture of acetic and propionic acid residues, a mixture of acetic and butyric acid residues, butyric acid, and a mixture of acetic, propionic, and butyric acid residues.

5. A method according to claim 4 wherein propionic acid residues predominate in the short chain component.

6. A method according to claim 4 wherein butyric acid residues predominate in the short chain component.

7. A method according to claim 4 wherein at least about 90% of the long acid residues are stearic acid residues.

8. A method according to claim 1 wherein the triglycerides are described by the formulae

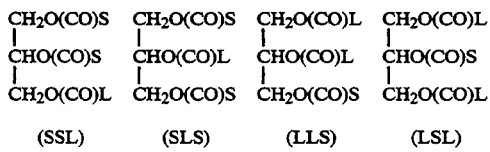

where
each L, independently, is a long chain saturated aliphatic group having between 15 and 21 carbons, derived from fatty acids having 16 and 22 carbons; and each S, independently, is a short chain group having 1 to 3 carbons, derived from a mixture of acids having 2 to 4 carbons, and wherein at least about 60 to about 70 mole % of the groups in the total triglyceride mixture are short chain groups.

9. A method according to claim 8 wherein at least about 64 to about 67 mole % of the groups in the total triglyceride mixture are short chain groups.

10. A method according to claim 9 wherein at least about 75% of the long chain group are stearic acid residues.

11. A method for controlling spread in cookies containing an ingredient that promotes spread comprising formulating the cookie dough with a shortening comprising geometry-altering triglycerides bearing a mixture of both long $C_{16}$ to $C_{22}$ saturated fatty acid residues and a mixture of short $C_2$ to $C_4$ acid residues and having a solid fat index between 15° and 30° C. of about 10% to about 70%, added to the cookie dough in amounts effective to reduce spread by use of said triglycerides.

12. A method according to claim 11 wherein said triglycerides have a solid fat index between 15° and 30° C. of about 30% to about 40%.

13. A method according to claim 11 wherein at least about 75% of said long residues are stearic acid residues and the short residues are a mixture of about 10% to 40% acetic acid residues and about 60% to 90% propionic acid residues.

14. A method according to claim 13 wherein at least about 90% of said long residues are stearic acid residues and the short residues are a mixture of about 10% to 15% acetic acid residues and about 85% to 90% propionic acid residues.

15. A method according to claim 11 wherein at least about 75% of said long residues are stearic acid residues and the short residues are a mixture of about 15% to about 20% acetic acid residues, about 35% to about 45% propionic acid residues, and about 35% to about 45% butyric acid residues.

16. A method according to claim 15 wherein at least about 90% of said long residues are stearic acid residues and the short residues are a mixture of about 20% acetic acid residues, about 40% propionic acid residues, and about 40% butyric acid residues.

17. A method according to claim 11 wherein the ingredient that promotes spread is selected from the group consisting of shredded coconut, coarse oats, oatmeal without fines, polyunsaturated fat, and polydextrose.

18. A method according to claim 17 wherein the ingredient that promotes spread is a polyunsaturated fat or polydextrose.

19. A method for controlling spread in cookies containing polydextrose comprising formulating the cookie dough with a shortening comprising geometry-altering triglycerides bearing both a mixture of long $C_{16}$ to $C_{22}$ saturated fatty acid residues and a mixture of short $C_2$ to $C_4$ acid residues, and having a solid fat index between about 15° and 30° C. of about 10% to about 70%, added to the cookie dough in amounts effective to reduce spread by use of said triglycerides.

* * * * *